United States Patent
Peng et al.

(10) Patent No.: US 11,593,935 B2
(45) Date of Patent: Feb. 28, 2023

(54) DOPAMINE TRANSPORTER CHECK SYSTEM AND OPERATION METHOD THEREOF

(71) Applicant: Taipei Medical University (TMU), Taipei (TW)

(72) Inventors: Syu-Jyun Peng, Zhubei (TW); Hsin-Yung Chen, Taoyuan (TW); Ya-Ju Tsai, Taipei (TW)

(73) Assignee: TAIPEI MEDICAL UNIVERSITY (TMU), Taipei (TW)

( * ) Notice: Subject to any disclaimer, the term of this patent is extended or adjusted under 35 U.S.C. 154(b) by 247 days.

(21) Appl. No.: 17/116,254

(22) Filed: Dec. 9, 2020

(65) Prior Publication Data

US 2022/0122246 A1    Apr. 21, 2022

(30) Foreign Application Priority Data

Oct. 15, 2020    (TW) .................................. 109135782

(51) Int. Cl.
*G06T 7/00*    (2017.01)
*G06T 7/33*    (2017.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC combination set(s) only.
See application file for complete search history.

(56) References Cited

U.S. PATENT DOCUMENTS

2021/0228144 A1* 7/2021 Hernandez ........... G01R 33/483
2022/0273184 A1* 9/2022 Clark .................... A61B 5/4082

FOREIGN PATENT DOCUMENTS

CN    105938617 A    9/2016
JP    2019045193 A    3/2019
(Continued)

OTHER PUBLICATIONS

Lycksam, Andreas "Automated diagnosis of degenerative diseases from images of the brain" Uppsala Universitet. Mar. 2, 2020 (Year: 2020).*

(Continued)

*Primary Examiner* — Molly Wilburn

(57) ABSTRACT

The present disclosure provides an operating method of a dopamine transporter check system, and the operation method includes steps as follows. A scan image of a subject's brain is obtained from a scan machine, and the scan image is a three-dimensional image. The scan image is aligned to a standard brain space to obtain a standardized scan image. Intensity normalization is performed on the standardized scan image. The standardized scan image after the intensity normalization is converted into a two-dimensional image. A plurality of image data are got from at least one region of interest in the two-dimensional image, and the at least one region of interest includes a left caudate, a left putamen, a right caudate and a right putamen. A dopamine neuron loss degree measurement and evaluation model based on the image data is established through a transfer learning.

10 Claims, 2 Drawing Sheets

(51) Int. Cl.
*A61B 5/055* (2006.01)
*A61B 5/00* (2006.01)

(52) U.S. Cl.
CPC ...... *G06T 7/33* (2017.01); *G06T 2207/10088* (2013.01); *G06T 2207/20081* (2013.01); *G06T 2207/30016* (2013.01)

(56) References Cited

FOREIGN PATENT DOCUMENTS

| | | |
|---|---|---|
| TW | I587841 | 6/2017 |
| TW | I686178 B | 3/2020 |

OTHER PUBLICATIONS

Quan, Justin "DaTscan SPECT Image Classification for Parkinson's Disease" arXiv:1909.04142 (Year: 2019).*

Choi, Hongyoon, et al., "Refining diagnosis of Parkinson's disease with deep learning-based interpretation of dopamine transporter imaging", NeuroImage: Clinical 16, 2017, 586-594.

Wenzel, Markus, et al., "Automatic classification of dopamine transporter SPECT: deep convolutional neural networks can be trained to be robust with respect to variable image characteristics", European Journal of Nuclear Medicine and Molecular Imaging, 2019, 2800-2811.

Mageshe, Rajkumar Pavan, et al., "An Explainable Machine Learning Model for Early Detection of Parkinson's Disease using LIME on DaTscan Imagery", Computers in Biology and Medicine, Aug. 4, 2020, p. 1-21.

Wingate, James, et al., "Unified deep learning approach for prediction of Parkinson's disease", IET Image Processing, vol. 14, Issue 10, Aug. 21, 2020, p. 1980-1989.

* cited by examiner

DOPAMINE TRANSPORTER CHECK SYSTEM AND OPERATION METHOD THEREOF

RELATED APPLICATIONS

This application claims priority to Taiwan Patent Application No. 109135782, filed Oct. 15, 2020, the entirety of which is herein incorporated by reference.

BACKGROUND

Field of Invention

The present invention relates to systems and operation methods, and more particularly, a dopamine transporter check system and an operating method thereof.

Description of Related Art

Parkinson's disease (PD) is a chronic neurodegenerative disease that affects the central nervous system, mainly affecting the motor nervous system. This symptom usually appears slowly over time. The most obvious early symptoms are tremor, stiffness of the limbs, decreased motor function and abnormal gait, and may also be accompanied by cognitive and behavioral problems. The main pathological changes of Parkinson's disease occur in the dense substantia nigra of the midbrain. This area contains a large number of dopamine neurons and transmits messages to the basal nucleus of the brain. The main symptoms of Parkinson's disease are caused by the degeneration of dopamine neurons in the substantia nigra compact area.

In clinical practice, Parkinson's disease is a common disease, but sometimes it is difficult to diagnose. After detailed observation and consultation, doctors need to perform imaging examinations such as magnetic resonance imaging or nuclear Medical dopamine transporter scan (e.g., dopamine transporter scan, DaT Scan) is used to distinguish Parkinson's disease patients from Parkinson's syndrome (Parkinsonisim).

The nuclear medicine examination is a functional imaging examination, which mainly uses visual reading and semi-quantitative specific binding ratio analysis for imaging diagnosis. However, visual reading may produce a certain degree of difference in the interpretation results due to ambient lighting, the brightness and contrast of screen displays, the fatigue of the human eyes and the judgement of different experiences.

SUMMARY

In one or more various aspects, the present disclosure is directed to a dopamine transporter check system and an operating method thereof.

An embodiment of the present disclosure is related to a dopamine transporter check system includes a memory circuit and a processor, the processor is electrically connected to the memory circuit. The memory circuit is configured to store at least one instruction. The processor is configured to access and execute the at least one instruction for: obtaining a scan image of a subject's brain from a scan machine, and the scan image being a three-dimensional image; aligning the scan image to a standard brain space to obtain a standardized scan image; performing an intensity normalization on the standardized scan image; converting the standardized scan image after the intensity normalization into a two-dimensional image; getting a plurality of image data from at least one region of interest in the two-dimensional image, and the at least one region of interest comprising a left caudate, a left putamen, a right caudate and a right putamen; establishing a dopamine neuron loss degree measurement and evaluation model based on the image data through a transfer learning.

In one embodiment of the present disclosure, the processor accesses and executes the at least one instruction for: obtaining a three-dimensional magnetic resonance image of the subject's brain from a magnetic resonance instrument; spatially aligning the scan image to the three-dimensional magnetic resonance image; getting a caudate and putamen deep gray matter structure from the three-dimensional magnetic resonance image; performing a spatial normalization on the spatially aligned scan image and the caudate and putamen deep gray matter structure through the three-dimensional magnetic resonance image, so that the spatially aligned scan image and the caudate and putamen deep gray matter structure is aligned to the standard brain space.

In one embodiment of the present disclosure, the processor accesses and executes the at least one instruction for: generating the at least one region of interest based on the caudate and putamen deep gray matter structure.

In one embodiment of the present disclosure, the processor accesses and executes the at least one instruction for: calculating an average value of image intensity of an occipital lobe in the standardized scan image as a baseline, so as to perform the Intensity normalization on the standardized scan image.

In one embodiment of the present disclosure, the processor accesses and executes the at least one instruction for: performing a data augmentation on the image data, so as to balance the number of images in different neuron loss levels.

Another embodiment of the present disclosure is related to an operation method of a dopamine transporter check system, and the operation method includes steps of: obtaining a scan image of a subject's brain from a scan machine, and the scan image being a three-dimensional image; aligning the scan image to a standard brain space to obtain a standardized scan image; performing an intensity normalization on the standardized scan image; converting the standardized scan image after the intensity normalization into a two-dimensional image; getting a plurality of image data from at least one region of interest in the two-dimensional image, and the at least one region of interest comprising a left caudate, a left putamen, a right caudate and a right putamen; establishing a dopamine neuron loss degree measurement and evaluation model based on the image data through a transfer learning.

In one embodiment of the present disclosure, the operation method further includes steps of obtaining a three-dimensional magnetic resonance image of the subject's brain from a magnetic resonance instrument; spatially aligning the scan image to the three-dimensional magnetic resonance image; getting a caudate and putamen deep gray matter structure from the three-dimensional magnetic resonance image; performing a spatial normalization on the spatially aligned scan image and the caudate and putamen deep gray matter structure through the three-dimensional magnetic resonance image, so that the spatially aligned scan image and the caudate and putamen deep gray matter structure is aligned to the standard brain space.

In one embodiment of the present disclosure, the operation method further includes a step of generating the at least one region of interest based on the caudate and putamen deep gray matter structure.

In one embodiment of the present disclosure, the step of performing the Intensity normalization on the standardized scan image includes calculating an average value of image intensity of an occipital lobe in the standardized scan image as a baseline, so as to perform the Intensity normalization on the standardized scan image.

In one embodiment of the present disclosure, the operation method further includes a step of performing a data augmentation on the image data, so as to balance the number of images in different neuron loss levels.

Technical advantages are generally achieved, by embodiments of the present disclosure. The present disclosure establishes a classification and grading model (i.e., the dopamine neuron loss degree measurement and evaluation model), so that the image is classified at the most probable stage of neuron loss, and provide physicians with an additional auxiliary diagnosis mode whenever the interpretation of each dopamine transporter examination, so as to improve the diagnosis rate and treatment results.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
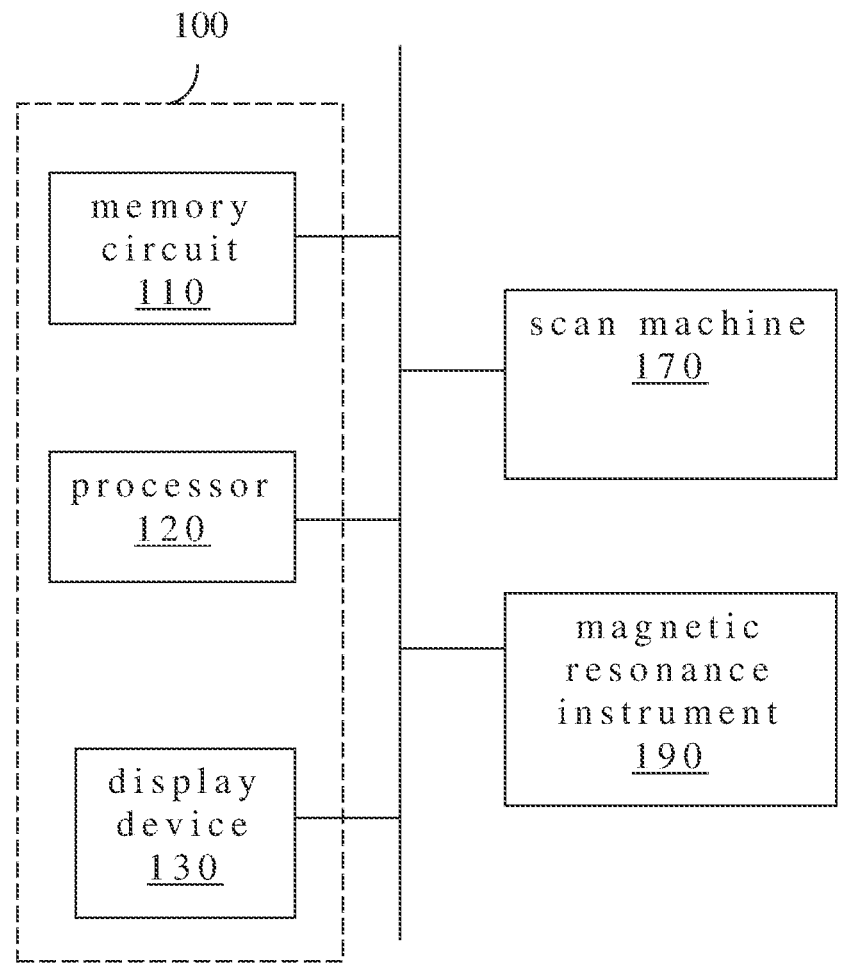
FIG. 1 is a block diagram of a dopamine transporter check system according to some embodiments of the present disclosure.

Reference will now be made in detail to the present embodiments of the invention, examples of which are illustrated in the accompanying drawings. Wherever possible, the same reference numbers are used in the drawings and the description to refer to the same or like parts.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram of a dopamine transporter check system 100 according to some embodiments of the present disclosure. As shown in FIG. 1, in some embodiments, the dopamine transporter check system 100 can include a memory circuit 110, a processor 120 and a display device 130. For example, the memory circuit 110 can be a hard drive, a flash memory or another storage device, the processor 120 can be a central processing unit, and a display device 130 can be a built-in the display screen or an external screen.

In structure, the dopamine transporter check system 100 is electrically connected to a scan machine 170 and a magnetic resonance instrument 190. The memory circuit 110 and the display device 130 are electrically connected to the processor 120. For example, the scan machine 170 can be a positron tomography scanner, a single photon emission computed tomography scanner, a computed tomography scanner, or a combination thereof.

In use, the memory circuit 110 is configured to store at least one instruction. The processor 120 is configured to access and execute the at least one instruction for: obtaining a scan image of a subject's brain from the scan machine 170, where the scan image is a three-dimensional image; aligning the scan image to a standard brain space (e.g., a Montreal Neurological Institute space) to obtain a standardized scan image; performing an Intensity normalization on the standardized scan image; converting the standardized scan image after the intensity normalization into a two-dimensional image; getting a plurality of image data from at least one region of interest in the two-dimensional image, and the at least one region of interest comprising a left caudate, a left putamen, a right caudate and a right putamen; establishing a dopamine neuron loss degree measurement and evaluation model (e.g., a classification and grading model) based on the image data through a transfer learning.

In one embodiment of the present disclosure, the processor 120 accesses and executes the at least one instruction for: obtaining a three-dimensional magnetic resonance image of the subject's brain from the magnetic resonance instrument 190; spatially aligning the scan image to the three-dimensional magnetic resonance image; getting a caudate and putamen deep gray matter structure from the three-dimensional magnetic resonance image; performing a spatial normalization on the spatially aligned scan image and the caudate and putamen deep gray matter structure through the three-dimensional magnetic resonance image, so that the spatially aligned scan image and the caudate and putamen deep gray matter structure can be aligned to the standard brain space.

Alternatively, In another embodiment of the present disclosure, the magnetic resonance instrument 190 may be omitted from the dopamine transporter check system 100. The processor 120 accesses and executes the at least one instruction for: performing the spatial normalization on the spatially aligned scan image through a default image, so that the spatially aligned scan image can be aligned to the standard brain space. For example, the default image can be an average image of historical scanned images, a standard image pre-loaded when the scan machine 170 is shipped from the factory, or an image made based on inspection experience.

In one embodiment of the present disclosure, the processor 120 accesses and executes the at least one instruction for: generating the at least one region of interest based on the caudate and putamen deep gray matter structure.

In one embodiment of the present disclosure, the processor 120 accesses and executes the at least one instruction for: calculating an average value of image intensity of an occipital lobe in the standardized scan image as a baseline, so as to perform the Intensity normalization on the standardized scan image. In practice, the image of the occipital lobe is relatively uniform; using this as a baseline can improve the accuracy of classification the dopamine transporter check system 100.

In one embodiment of the present disclosure, the processor accesses and executes the at least one instruction for: performing a data augmentation on the image data, so as to balance the number of images in different neuron loss levels. For example, if there is too less data of one or several neuron loss levels in the image data (for example, the ratio of the aforesaid less data to the most data of a neuron loss level is lower than a preset ratio), the aforesaid less data of one or several neuron loss levels can be augmented (such as rotating and shifting images), so that the amount of data of each neuron loss level is roughly the same, so as to achieve an efficiently training model of the transfer learning.

In practice, the brain dopamine transporter examination (DaT Scan) is for patients with Parkinson's syndrome (Parkinsonisim), and the diagnosis of Parkinson's disease is based on the degree of uptake of the basal nucleus to the radiopharmaceutical disease. In the scan images of normal patients obtained by the scan machine 170, because the number of dopamine neurons is normal, it can be seen that the two sides of the basal nucleus normally take up the radioactive tracer on the image. In the scan images of Parkinson's patients, because the number of dopamine neurons is reduced, the basal nucleus on the image produces the result of insufficient uptake of one-sided or two-sided radiotracer. However, this image difference is difficult to distinguish with the human eyes.

The dopamine transporter check system 100 uses transfer learning (such as deep convolutional neural network) due to the image data, so as to find out the characteristic of the patient's striatum in the image of the radioactive tracer intake, further subdivide the striatum into caudate and putamen, and then establishes a classification and grading model (i.e., the dopamine neuron loss degree measurement and evaluation model), so that the image is classified at the most probable stage of neuron loss, and provide physicians with an additional auxiliary diagnosis mode whenever the interpretation of each dopamine transporter examination, so as to improve the diagnosis rate and treatment results.

Figure 2:
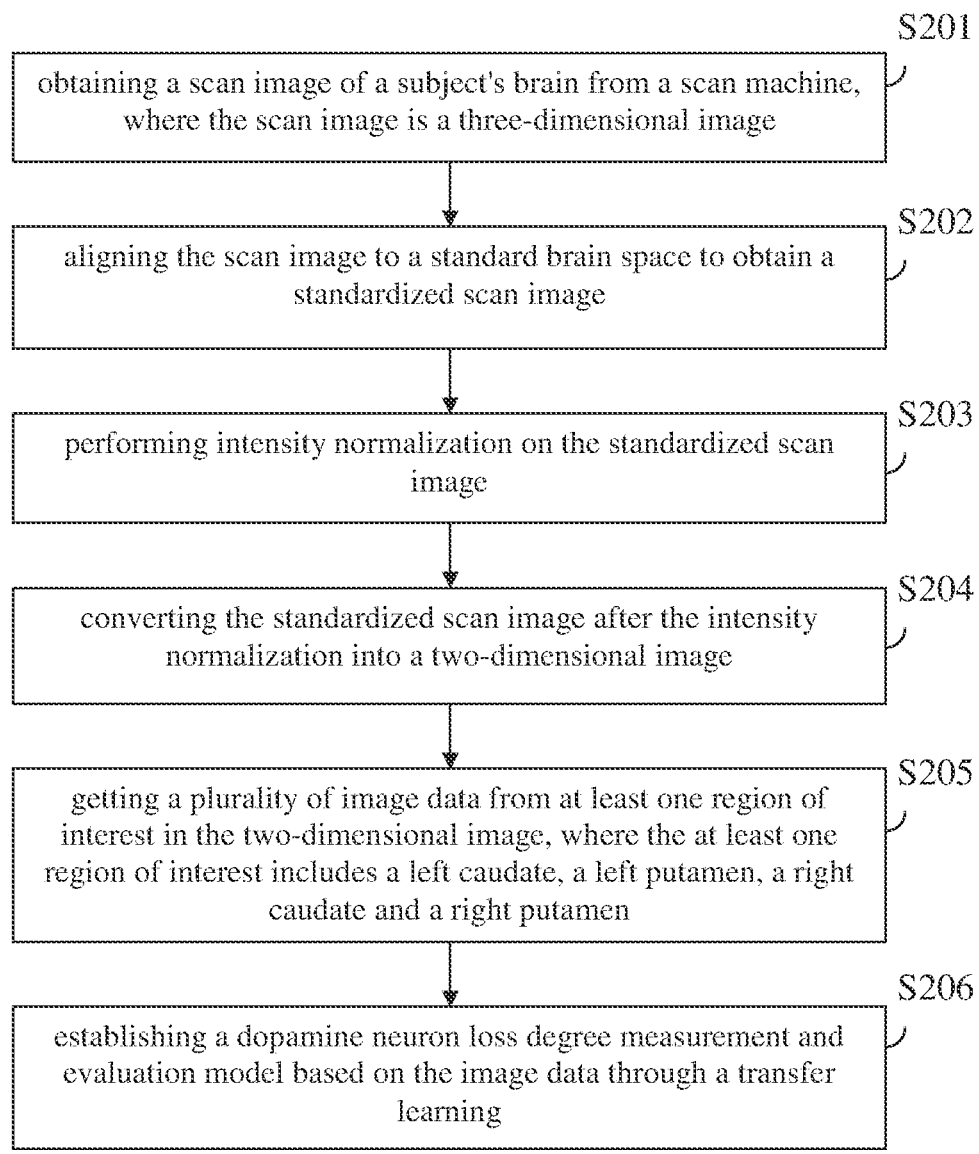
FIG. 2 is a flow chart of an operation method of the dopamine transporter check system according to some embodiments of the present disclosure.

For a more complete understanding of an operating method of the dopamine transporter check system 100, referring FIGS. 1-2, FIG. 2 is a flow chart of the operation method 200 of the dopamine transporter check system 100 according to one embodiment of the present disclosure. As shown in FIG. 2, the operation method 200 includes operations S201-S206. However, as could be appreciated by persons having ordinary skill in the art, for the steps described in the present embodiment, the sequence in which these steps is performed, unless explicitly stated otherwise, can be altered depending on actual needs; in certain cases, all or some of these steps can be performed concurrently.

In operation S201, a scan image of a subject's brain is obtained from the scan machine 170, where the scan image is a three-dimensional image. In operation S202, the scan image is aligned to a standard brain space to obtain a standardized scan image. In operation S203, the intensity normalization is performed on the standardized scan image. In operation S204, the standardized scan image after the intensity normalization is converted into a two-dimensional image. In operation S205, a plurality of image data are got from at least one region of interest in the two-dimensional image, where the at least one region of interest includes a left caudate, a left putamen, a right caudate and a right putamen. In operation S206, a dopamine neuron loss degree measurement and evaluation model based on the image data is established through the transfer learning.

In one embodiment of the present disclosure, the operation method 200 further includes steps of obtaining a three-dimensional magnetic resonance image of the subject's brain from a magnetic resonance instrument; spatially aligning the scan image to the three-dimensional magnetic resonance image; getting a caudate and putamen deep gray matter structure from the three-dimensional magnetic resonance image; performing a spatial normalization on the spatially aligned scan image and the caudate and putamen deep gray matter structure through the three-dimensional magnetic resonance image, so that the spatially aligned scan image and the caudate and putamen deep gray matter structure is aligned to the standard brain space.

In one embodiment of the present disclosure, the operation method 200 further includes a step of generating the at least one region of interest based on the caudate and putamen deep gray matter structure.

In one embodiment of the present disclosure, operation S203 includes further includes a step of calculating an average value of image intensity of an occipital lobe in the standardized scan image as a baseline, so as to perform the Intensity normalization on the standardized scan image.

In one embodiment of the present disclosure, the operation method 200 further includes a step of performing a data augmentation on the image data, so as to balance the number of images in different neuron loss levels.

Technical advantages are generally achieved, by embodiments of the present disclosure. The present disclosure establishes a classification and grading model (i.e., the dopamine neuron loss degree measurement and evaluation model), so that the image is classified at the most probable stage of neuron loss, and provide physicians with an additional auxiliary diagnosis mode whenever the interpretation of each dopamine transporter examination, so as to improve the diagnosis rate and treatment results.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:
1. A dopamine transporter check system, comprising:
a memory circuit configured to store at least one instruction; and
a processor electrically connected to the memory circuit, and the processor configured to access and execute the at least one instruction for:

obtaining a scan image of a subject's brain from a scan machine, and the scan image being a three-dimensional image;

aligning the scan image to a standard brain space to obtain a standardized scan image;

performing an intensity normalization on the standardized scan image;

converting the standardized scan image after the intensity normalization into a two-dimensional image;

getting a plurality of image data from at least one region of interest in the two-dimensional image, and the at least one region of interest comprising a left caudate, a left putamen, a right caudate and a right putamen; and establishing a dopamine neuron loss degree measurement and evaluation model based on the image data through a transfer learning.

2. The dopamine transporter check system of claim 1, wherein the processor accesses and executes the at least one instruction for:

obtaining a three-dimensional magnetic resonance image of the subject's brain from a magnetic resonance instrument;

spatially aligning the scan image to the three-dimensional magnetic resonance image;

getting a caudate and putamen deep gray matter structure from the three-dimensional magnetic resonance image; and performing a spatial normalization on the spatially aligned scan image and the caudate and putamen deep gray matter structure through the three-dimensional magnetic resonance image, so that the spatially aligned scan image and the caudate and putamen deep gray matter structure is aligned to the standard brain space.

3. The dopamine transporter check system of claim 2, wherein the processor accesses and executes the at least one instruction for:

generating the at least one region of interest based on the caudate and putamen deep gray matter structure.

4. The dopamine transporter check system of claim 1, wherein the processor accesses and executes the at least one instruction for:

calculating an average value of image intensity of an occipital lobe in the standardized scan image as a baseline, so as to perform the Intensity normalization on the standardized scan image.

5. The dopamine transporter check system of claim 1, wherein the processor accesses and executes the at least one instruction for:

performing a data augmentation on the image data, so as to balance the number of images in different neuron loss levels.

6. An operation method of a dopamine transporter check system, and the operation method comprising steps of:

obtaining a scan image of a subject's brain from a scan machine, and the scan image being a three-dimensional image;

aligning the scan image to a standard brain space to obtain a standardized scan image;

performing an intensity normalization on the standardized scan image;

converting the standardized scan image after the intensity normalization into a two-dimensional image;

getting a plurality of image data from at least one region of interest in the two-dimensional image, and the at least one region of interest comprising a left caudate, a left putamen, a right caudate and a right putamen; and establishing a dopamine neuron loss degree measurement and evaluation model based on the image data through a transfer learning.

7. The operation method of claim 6, further comprising:

obtaining a three-dimensional magnetic resonance image of the subject's brain from a magnetic resonance instrument;

spatially aligning the scan image to the three-dimensional magnetic resonance image;

getting a caudate and putamen deep gray matter structure from the three-dimensional magnetic resonance image; and performing a spatial normalization on the spatially aligned scan image and the caudate and putamen deep gray matter structure through the three-dimensional magnetic resonance image, so that the spatially aligned scan image and the caudate and putamen deep gray matter structure is aligned to the standard brain space.

8. The operation method of claim 7, further comprising:

generating the at least one region of interest based on the caudate and putamen deep gray matter structure.

9. The operation method of claim 6, wherein the step of performing the Intensity normalization on the standardized scan image comprises:

calculating an average value of image intensity of an occipital lobe in the standardized scan image as a baseline, so as to perform the Intensity normalization on the standardized scan image.

10. The operation method of claim 6, further comprising:

performing a data augmentation on the image data, so as to balance the number of images in different neuron loss levels.

* * * * *